United States Patent
García Alberola et al.

(10) Patent No.: US 8,868,171 B2
(45) Date of Patent: Oct. 21, 2014

(54) SYSTEM AND METHOD FOR RECONSTRUCTING AND VIEWING CARDIAC ELECTRICAL ACTIVATION

(75) Inventors: Arcadio García Alberola, El Palmar (ES); Juan José Sanchez Muñoz, El Palmar (ES); José Luis Rojo Alvarez, Fuenlabrada (ES); Felipe Alonso Atienza, Fuenlabrada (ES); Jesús Requena Carrion, Fuenlabrada (ES); Mark Richard Wilby, Fuenlabrada (ES); Antonio José Caamano Fernandez, Fuenlabrada (ES); Francisco Javier Ramos López, Fuenlabrada (ES); Miguel Ángel Moscoso Castro, Leganes (ES); Juan Diego Alvarez Román, Leganes (ES)

(73) Assignees: Universidad Carolos III de Madrid (ES); Fundacion para la Formacion e Investigacion Santarias de la Region de Murcia (ES); Universidad Rey Juan Carlos (ES)

( * ) Notice: Subject to any disclaimer, the term of this patent is extended or adjusted under 35 U.S.C. 154(b) by 828 days.

(21) Appl. No.: 12/988,230
(22) PCT Filed: Apr. 14, 2009
(86) PCT No.: PCT/ES2009/000194
§ 371 (c)(1), (2), (4) Date: Apr. 1, 2011
(87) PCT Pub. No.: WO2009/127755
PCT Pub. Date: Oct. 22, 2009

(65) Prior Publication Data
US 2011/0224526 A1 Sep. 15, 2011

(30) Foreign Application Priority Data
Apr. 15, 2008 (ES) .................... 200801074

(51) Int. Cl.
A61B 5/04 (2006.01)
A61B 5/0402 (2006.01)
A61B 5/042 (2006.01)
G06K 9/62 (2006.01)

(52) U.S. Cl.
CPC ............ *A61B 5/0402* (2013.01); *G06K 9/6269* (2013.01); *A61B 5/04012* (2013.01); *A61B 5/042* (2013.01)
USPC ........................................... 600/523; 600/512

(58) Field of Classification Search
USPC .................................................. 600/512, 523
See application file for complete search history.

(56) References Cited

U.S. PATENT DOCUMENTS

| 5,297,549 A | 3/1994 | Beatty et al. |
| 5,311,866 A | 5/1994 | Kagan et al. |
| 6,892,091 B1 | 5/2005 | Ben-Haim et al. |

FOREIGN PATENT DOCUMENTS

ES 2 265 395 2/2007

OTHER PUBLICATIONS

Torre. "Estudios Electrofisiologicos con Sistemas de Navegacion." *Entermeria en Cardiologia*. No. 36. vol. 3. 2005. pp. 40-44. Abstract Provided.

Trejo. "Las maquinas de vectores de sporte para identification en linea." 2006. English Summary provided.

*Primary Examiner* — Tammie K Heller
(74) *Attorney, Agent, or Firm* — Merchant & Gould P.C.

(57) ABSTRACT

System for reconstruction and visualization of cardiac electric activity, with high-resolution capabilities, which improves the performance of current systems by means of the inclusion of the a priori information of the bioelectric problem in a learning algorithm, and by means of the exploitation of the spatial and temporal correlations thanks to interpolation and decimation subsystems. The system consists of, at least: a plurality of catheters; ways for obtaining the location coordinates of said array; ways for obtaining the cardiac walls geometry; ways for processing the signals from the catheters, implementing an algorithm based on Support Vector Machines, allowing the incorporation of the bioelectric phenomena; ways of interpolation and redundance exploiting for yielding high resolution without matrix inversions; and ways of visualization.

10 Claims, 2 Drawing Sheets

SYSTEM AND METHOD FOR RECONSTRUCTING AND VIEWING CARDIAC ELECTRICAL ACTIVATION

This application is a National Stage Application of PCT/ES2009/000194, filed 14 Apr. 2009, which claims benefit of Serial No. P200801074, filed 15 Apr. 2008 in Spain and which applications are incorporated herein by reference. To the extent appropriate, a claim of priority is made to each of the above disclosed applications.

OBJECT OF THE INVENTION

The object of the present invention is a new system for reconstruction of the cardiac electric activity from cardiac electric signals recorded with a vector (array) of intracardiac catheters and adequate processing media. This invention permits the visualization of the position of cardiac electrical activity, which consist of estimating the endocardial or epicardial electric sources (transmembrane voltage or current) from remote measurements (intracardiac electrograms) in catheters or electrodes.

FIELD OF THE INVENTION

The field of the invention is that one of systems for generating and visualizing medical images, specifically, the graphical representation of the electric activity in medical systems used in electrocardiology and cardiac electrophysiology.

BACKGROUND OF THE INVENTION

Systems for the Inverse Problem in Cardiology.

Cardiac arrhythmias are one of the main causes of mortality in the world. Current therapies have their fundamentals on a partial knowledge of the mechanisms of the most usual arrhythmias (atrial and ventricular tachicardias, atrial and ventricular fibrillation, and others), and though these therapies reach high levels of effectiveness, the detailed knowledge of a fast arrhythmia (tachyarrhythmia) is the key for creating new anti-arrhythmic therapies or for improving the actual ones.

Nevertheless, the knowledge of the arrhythmic mechanism in a given patient is limited by the fact that the physical magnitude involved is the electric impulse propagation throughout the cardiac cells. The visualization of electric activity in the internal surface of the heart (endocardium) is troublesome, given that current technology only gives indirect measurements, consisting of electric voltage measured in catheters inside the heart (electrograms). These measurements record the electric field that is induced by the cardiac currents at a given distance of atrial or ventricular walls, and hence, mathematical calculations are required for estimated the numerical values of the cardiac currents in the endocardial surface.

Intracardiac navigation systems allow the spatial reconstruction of one or several cardiac cavities and a representation of myocardial electrical activity changes with time, using the electric signal recordings in diverse points and the detection of the spatial location of the catheter from different spatial location media. Currently, several cardiac navigation systems are used to reconstruct the cardiac electric activity in the myocardium from measurements in catheters. The most relevant are the following:

i. Carto System (Biosense, Cordis-Webster). It is probably the most widespread used. It allows to obtain an image (color-coded) of the relative activation time of the endocardium with respect to a reference signal during a stationary rhythm. Its main limitation is it only can be used in stationary rhythms, hence it can not be used in real time, for analyzing the nature of non-periodic arrhythmias. More, it requires a time for mapping the electric activity in each patient, between one and three hours, which represents a high cost for the health system.

ii. Localisa. This system is similar to the preceding one, and it was commercialized by Medtronic. It is no longer commercialized, and its successor is Navex (in the sense that it uses the same system for spatial detection).

iii. Ensite. It is an advanced system allowing the reconstruction of the myocardial electric activation from the recordings in a catheter array. Theoretically, it allows this reconstruction in an instantaneous form, hence being potentially useful for any kind of arrhythmia (periodical or not).

Probably, the reason why Ensite has not gained wider acceptance and use in practice, despite its theoretical advantages, is that it gives an estimation of bioelectrical currents with an associated uncertainty. Improvement of this uncertainty would make a system of this family having a widespread acceptation in the clinical practice. Other problems are the catheters dimensions, its complicated manipulation, its price, and the fact that the accurate information is limited to the proximal zone of the electrode.

In the current state of technique, several systems are described including the use of catheters for cardiac mapping. Among them, we can consider the patents U.S. Pat. No. 6,892,091, U.S. Pat. No. 5,297,549, and U.S. Pat. No. 5,311,866.

DESCRIPTION OF THE INVENTION

The system for the reconstruction and visualization of cardiac electric activity, object of the present invention, may include, at least:

a. A set of intracardiac catheters.
b. Media for positioning and obtaining the location coordinates of said set.
c. Media for auxiliary image (resonance, CAT, echography, scopy) that yields the geometrical coordinates of the cardiac wall, and eventually of some additional electric properties (for instance, necrosis regions).
d. Media for processing the signals from the catheters, where said processing methods include, at least, an algorithm based on SVM for the reconstruction of the dual signal problem.
e. Media for visualizing the processed signals.
f. Media for making use of spatial redundancy and improving the resolution without needing Matrix inversion.

Where the SVM subsystem includes a statistical learning algorithm that is derived from the structural risk minimization principle. Two of the main advantages of the SVM are regularization and robustness, which are ideal conditions for the requirements of the inverse problem in electrocardiography.

The said system generates a plurality of signals whose physical origin is in that system, and they are subsequently used in the method, hence we have that:

Signals v[k] are the voltages measured in the k-th electrode of the catheter set, and they are acquired in the same time instant for all the electrodes.
Signal ho[k] is the spatial transfer function, and it can be either estimated by conventional system identification techniques, or obtained from the volume conductor equation for a homogeneous media.

Spatial coordinates of each catheter are recorded by means of available media of catheter positioning.

Data of the cardiac cavity geometry are obtained with the auxiliary image subsystem, from image fusion techniques from previous medical images, such as magnetic resonance (and variants) or ultrasound echocardiography.

A second aspect of the present invention is the method for reconstruction and visualization of cardiac activity that includes, at least, the next stages:

(i) A first stage of registering the anatomical cardiac information (resonance, ultrasound) and storing it in digital format.

(ii) A second stage of electro-physiological procedure, where a set of catheters are placed inside the cavity, and the catheter locations are recorded with the dedicated subsystem.

(iii) A third stage of calculating the distance matrix, with the previous information, storing it in digital format.

(iv) A fourth stage of simultaneously recording of the voltages in the catheters v[k], for k successive time instants.

(v) For each voltage measurement v[k], the SVM is volved in a digital processing element as follows:
   a. The quadratic problem given by measurements v[k] and by the distance matrix is solved in block, and transmembrane currents i[k] are estimated.
   b. The signal of measurements of estimated voltages v[k] is interpolated, from estimated transmembrane currents i[k].
   c. Interpolated potentials are checked to correspond with quality to the recorded potentials.

(vi) A sixth stage (optional) of visualization of the reconstructed voltage (with increased resolution) or of the estimated transmembrane current (with increase resolution) for successive time instants.

BRIEF DESCRIPTION OF THE DRAWINGS

We next describe (very briefly) a series of plots which aim to help to better understand the invention, and that are related with a realization of said invention that is presented as a non-limiting example.

PREFERRED EMBODIMENT OF THE INVENTION

The system for reconstruction and visualization of cardiac electric activity, object of the present invention, may include at least:

a. A set of intracardiac catheters.
b. Media for positioning for obtention of the location coordinates of said set.
c. Media for auxiliary image (resonance, CAT, echocardiography, scopy) yielding the location coordinates for the cardiac wall geometry, and eventually of some additional electrical properties (for instance, necrosed regions).
d. Media for processing the signals from the set of intracardiac catheters, where said media include at least an algorithm based on SVM for solving the dual signal problem.
e. Media for visualization of the processed signal.
f. Media for making use of spatial redundancy and improving the resolution without needing Matrix inversion.

Where the SVM subsystem consists of a statistical learning algorithm derived from the structural risk minimization principle. Two of the main advantages of the sVM are regularization and robustness, ideal conditions for the requirements of the inverse problem in electrocardiography.

Said system generates a plurality of signals with physical origin on that system, and they are subsequently used, hence, we have that:

Signals v[k] are the voltages measured in the k-th element of the set of catheters, and they are acquired at the same time instant for all the catheters.

Signal ho[k] is the spatial transfer function, and it can be either estimated from conventional system identification techniques, or given by the volume conductor equation for a homogeneous media.

Spatial coordinates of each catheter are recorded with the location media of the catheters.

Data about the cardiac cavity geometry are obtained with the auxiliary medical image media, thanks to fusion image techniques from previous medical images, such as given by magnetic resonance, or by ultrasound echocardiography.

Figure 1:
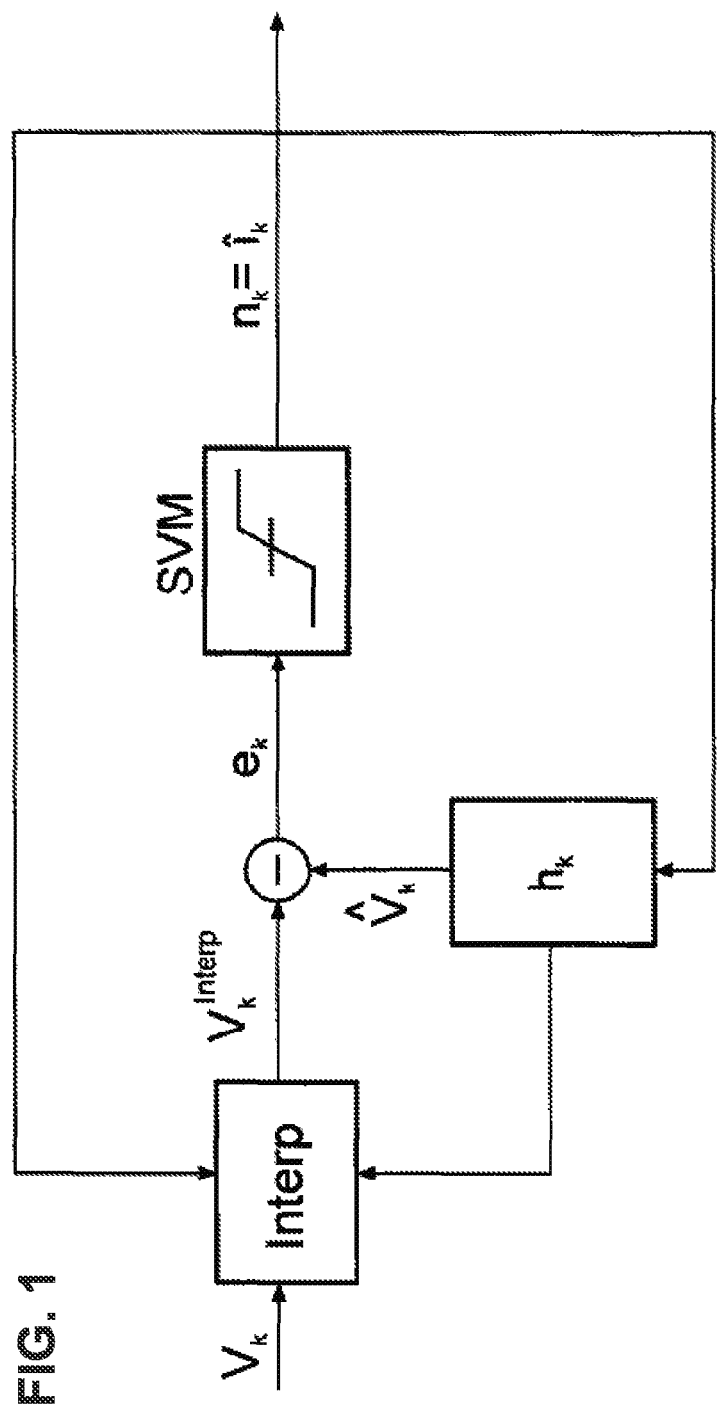
FIG. 1.—Block diagram of the system for reconstruction and visualization of cardiac electric activity, object of the present invention.

In FIG. 1 we can observe the block diagram of the system, where it has been included an interpolation/decimation stage for obtaining an increment in resolution given by a number of sensing catheters.

A second aspect of the present invention is the method of reconstruction and visualization of the cardiac activity, which includes, at least, the following stages:

(i) A first stage of registering the anatomical cardiac information (resonance, ultrasound, or others) and storing it in digital format.

(ii) A second stage of electro-physiological procedure, where a set of catheters are placed inside the cavity, and the catheter locations are recorded with the dedicated subsystem.

(iii) A third stage of calculating the distance matrix, with the previous information, storing it in digital format, and building the SVM kernel from it.

(iv) A fourth stage of simultaneously recording of the voltages in the catheters v[k], for k successive time instants.

(v) For each voltage measurement v[k], the SVM is volved in a digital processing element as follows:
   a. The quadratic problem given by measurements v[k] and by the distance matrix is solved in block, and transmembrane currents i[k] are estimated.
   b. The signal of measurements of estimated voltages v[k] is interpolated, from estimated transmembrane currents i[k].
   c. Interpolated potentials are checked to correspond with quality to the recorded potentials.

(vi) A sixth stage (optional) of visualization of the reconstructed voltage (with increased resolution) or of the estimated transmembrane current (with increase resolution) for successive time instants.

The SVM stage, which is the responsible of restoring the electric cardiac activity, is described more in detail with a set of equations which are necessary for defining said stage.

i. Signal Model.

The voltage sensing in catheters, for a given time instant, can be written as:

$$egm(t_0) = M \cdot i_m(t_0)$$

where M represents the distance matrix relating (according to the volume conductor model) the transmembrane current ($i_m$) with the voltage that is recorded in different points of the cardiac substrate (egm). In matrix form:

$$egm(t_0) = M \cdot i_m(t_0) \Rightarrow v = H \cdot i \Rightarrow v = i^T \cdot H$$

where v is a [K×1] matrix, i is a [L×1] matrix, and H is a [L×K] matrix, with L≥K. Explicitly, we have:

$$\begin{bmatrix} v_0 \\ \vdots \\ v_{k-1} \end{bmatrix} = [i_0, i_1, \ldots, i_{L-1}]^T \cdot [h_0, h_1, \ldots, h_{K-1}]$$

Figure 2:
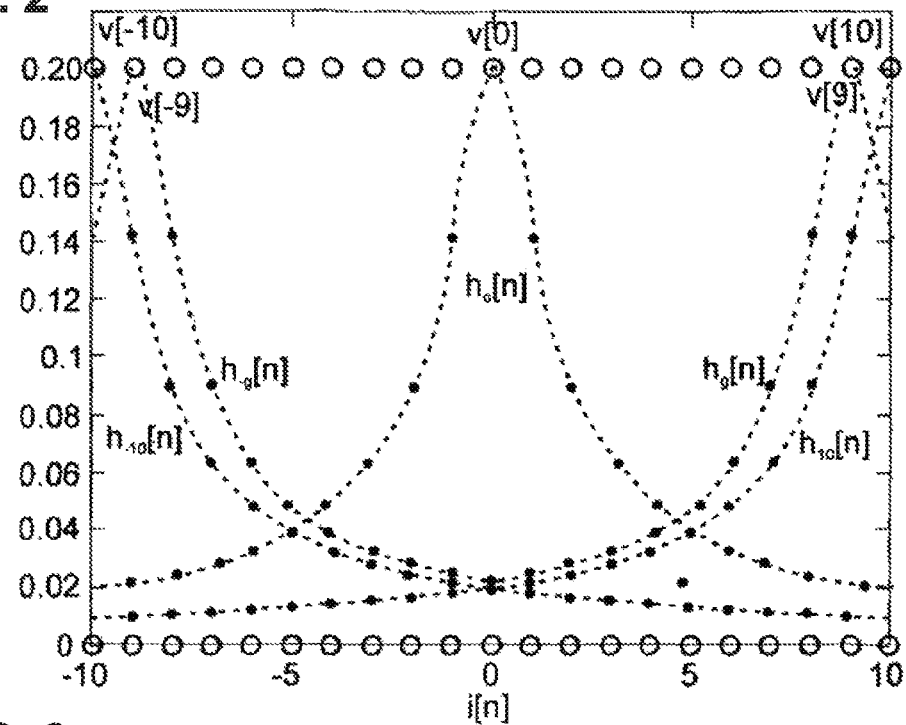
FIG. 2.—Representation of a unidimensional simulation of the system for reconstruction and visualization of the cardiac electrical activity, object of the present invention.
Figure 3:
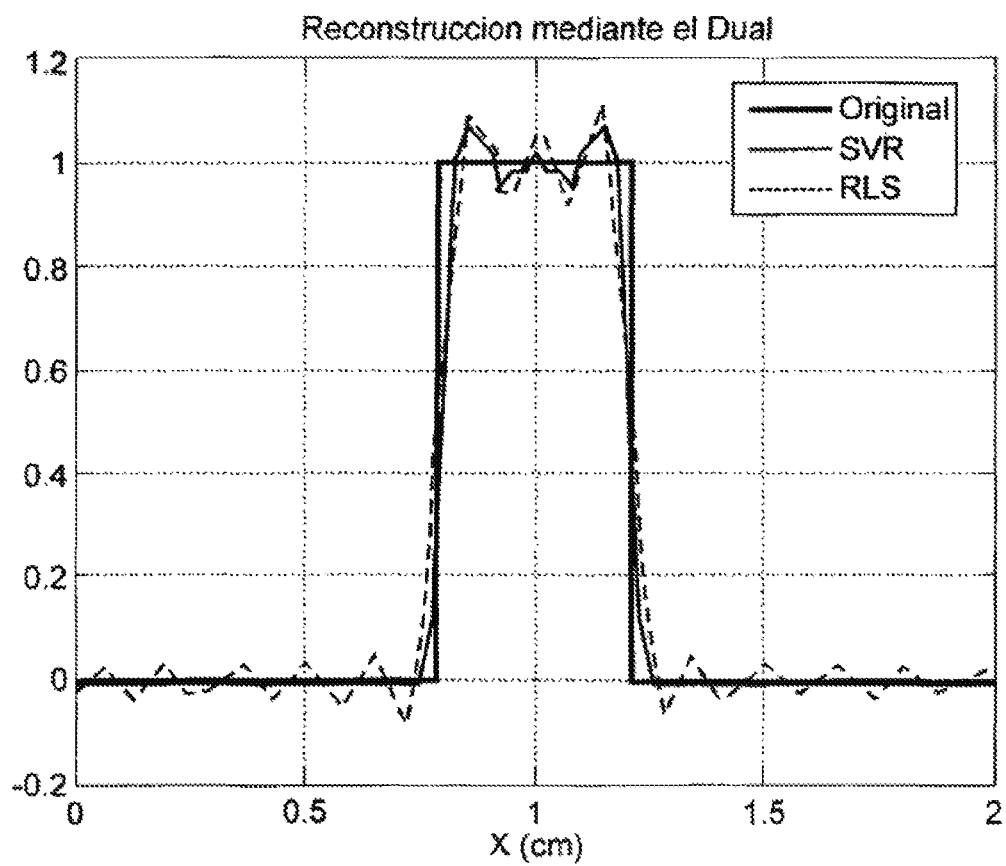
FIG. 3.—Reconstruction of the signal of the system for reconstruction and visualization of cardiac electric activity, object of the present invention.

In FIG. 2 we show the unidimensional representation of the electrode measurements recording, where $h_k$ is distance matrix M (expressed in vector form) that relates the transmembrane current in each myocite with the voltage measured in the k-th electrode. For electrode k, the captation model can be written as:

$$v_k = \sum_{l=0}^{L-1} i_l h_{lk} = i^T \cdot h_k.$$

where (·) denotes the dot product. This function is also depicted in FIG. 2. This equation, in conventional notation for signal processing, is defined as:

$$v[k] = \sum_{n=0}^{K-1} i[n] \cdot h_k[n].$$

Given that $h_k[n]$ can be expressed as $h_0[n-k]$, and by defining the impulse response as $h[n]=h_0[n]$, the system is perfectly characterized by the convolution between the current and transfer function h[n]:

$$[k] - \sum_{n=0}^{K-1} i[n] \cdot h_k[n] = \sum_{n=0}^{K-1} i[n] \cdot h[n-k] = i[k] * h[k]$$

The problem of cardiac activity reconstruction, as shown next, consists then in finding that current i[k] better approximating the voltage measured in the exterior points of the volume conductor v[k].

ii. Signal Model in the Primal Problem

Be the truncated time series $\{v_k, k=0, \ldots, K-1\}$ the set of values of voltage observed as a result of convolving the unknown time series of the myocites currents $\{i_k, k=0, \ldots, K-1\}$ with the known transfer function $\{h_k, k=0, \ldots, K-1\}$, so that the next model is obtained:

$$v_k = \hat{i} * h_k + e_k = \sum_{n=0}^{K-1} i_n h_{n-k} + e_k$$

Where the problem of current estimation can be expressed as the minimization of:

$$J_{PSM} = \frac{1}{2} \|\hat{i}\|_2^2 + \sum_{k=0}^{K-1} L^{\in H}(e_k)$$

Where $\bar{I} = [i_0, \ldots i_{k-1}]^T$ and:

$$L^{\in H}(e_k) = \begin{cases} 0, & |e_k| \leq \varepsilon \\ \frac{1}{2\delta}(|e_k| - \varepsilon)^2, & \varepsilon \leq |e_k| \leq e_C \\ C(|e_k| - \varepsilon) - \frac{1}{2}\delta C^2, & |e_k| \geq e_C \end{cases}$$

Therefore, the previous functional can be expressed as:

$$J_{PSM} = \sum_{k=0}^{K-1} \frac{i_k^2}{2} + \frac{1}{2\delta} \sum_{k \in I_1} (\xi_k^2 + \xi_k^{*2}) + C \sum_{k \in I_2} (\xi_k + \xi_k^*) - \frac{1}{2} \sum_{k \in I_2} \delta C^2$$

Which has to be minimized with respect to $\{i_k\}$ and $\{\epsilon^{(*)}{}_k\}$, constrained to:

$$v_k - \sum_{j=0}^{K-1} i_j h_{k-j} \leq \varepsilon + \xi_k$$

$$-v_k + \sum_{j=0}^{K-1} i_j h_{k-j} \leq \varepsilon + \xi_k^*$$

$$\xi_k, \xi_k^* \geq 0$$

For k=0, ..., k−1 and where $\{\epsilon^{(*)}{}_k\}$ are slack variables or losses, and $I_1$ ($I_2$) are the indices of the residuals that can be found in the quadratic (linear) cost zone.

The solution to the previous optimization problem is given by the saddle point of the corresponding Lagrangian function:

$$L = \sum_{k=0}^{K-1} \frac{i_k^2}{2} + \frac{1}{2\delta} \sum_{k \in I_1} (\xi_k^2 + \xi_k^{*2}) + C \sum_{k \in I_2} (\xi_k + \xi_k^*) -$$

$$\frac{1}{2} \sum_{k \in I_3} \delta C^2 - \sum_{k=0}^{K-1} (\beta_k \xi_k + \beta_k^* \xi_k^*) + + \sum_{k=0}^{K-1} \alpha_k \left( v_k - \sum_{j=0}^{K-1} i_j h_{k-j} - \varepsilon - \xi_k \right) +$$

$$\sum_{k=0}^{K-1} \alpha_k^* \left( -v_k + \sum_{j=0}^{K-1} i_j h_{k-j} - \varepsilon - \xi_k^* \right)$$

subject to the following constraints:

$$\alpha_k^{(*)}, \beta_k^{(*)}, \xi_k^{(*)} \geq 0$$

$$\frac{\partial L}{\partial i_n} = 0;$$

$$\frac{\partial L}{\partial \xi_n^{(*)}} = 0$$

together with Karush-Kuhn-Tucker conditions:

$$\begin{cases} \alpha_k \left( v_k - \sum_{j=0}^{K-1} i_j h_{k-j} - \varepsilon - \xi_k \right) = 0 \\ \alpha_k^* \left( -v_k + \sum_{j=0}^{K-1} i_j h_{k-j} - \varepsilon - \xi_k^* \right) = 0 \end{cases}$$

$$\begin{cases} \beta_k \xi_k = 0 \\ \beta_k^* \xi_k^* = 0 \end{cases}$$

Since $\{\epsilon_k^{(*)}\}$ are slack variables, then $\epsilon_k \epsilon_k^* = 0$, and therefore $\alpha_k \alpha_k^* = 0$. By deriving the Lagrangian with respect to the primal variables, we can obtain the dual problem, which is the next stage of the method.

iii. Signal Model in the Dual Problem $$\frac{\partial L}{\partial i_n} = 0:$$

For the optimization of $$i_n - \frac{\partial \left[ \sum_{k=0}^{K-1} (\alpha_k - \alpha_k^*) \left( \sum_{n=0}^{K-1} i_n h_{k-n} \right) \right]}{\partial i_n} = 0 \Rightarrow i_n = \sum_{k=0}^{K-1} (\alpha_k - \alpha_k^*) h_{k-n}$$

Using a change of variables and having $n_j = \alpha_j - \alpha_j^*$, we have:

$$\hat{i}_k = \sum_{j=0}^{K-1} h_{j-k}(\alpha_j - \alpha_j^*) = h_{-k} * \eta_k$$

which can be expressed in matrix form as:

$$\hat{i} = \sum_{j=0}^{K-1} h_{j-k}(\alpha_j - \alpha_j^*)$$

where $h_{j-k} = [1 \times K]$, and hence $$\hat{i} = H(\alpha - \alpha^*)$$

where $H(m,p) = h_{p-m}$ with indices $\{m, p = 1, \ldots, K\}$ and hence:

$$\begin{bmatrix} h_0 & h_1 & \ldots & h_{K-1} \\ h_{-1} & h_0 & \ldots & h_{K-2} \\ \vdots & \vdots & \ddots & \vdots \\ h_{1-K} & h_{2-K} & \ldots & h_0 \end{bmatrix}$$

Moreover, given that $$\|i\|^2 = i^T i = \|i\|^2 = (\alpha - \alpha^*)^T H^T H (\alpha - \alpha^*)$$

$$\|i\|^2 = (\alpha - \alpha^*)^T K (\alpha - \alpha^*)$$

$$K = H^T H$$

Explicitly, $$K = \begin{bmatrix} h_0 & h_{-1} & \ldots & h_{1-K} \\ h_1 & h_0 & \ldots & h_{2-K} \\ \vdots & \vdots & \ddots & \vdots \\ h_{K-1} & h_{K-2} & \ldots & h_0 \end{bmatrix} \cdot \begin{bmatrix} h_0 & h_1 & \ldots & h_{K-1} \\ h_{-1} & h_0 & \ldots & h_{K-2} \\ \vdots & \vdots & \ddots & \vdots \\ h_{1-K} & h_{2-K} & \ldots & h_0 \end{bmatrix}$$

which can be expressed in a compressed form as $$K(m,p) = \sum_{z=1}^{K} h_{m-z} h_{p-z}$$

where m, p, z are indices taking values in $\{1, \ldots, K\}$, and taking $n = m - p$, previous equation can be written as:

$$K(n,p) = \sum_{z=1}^{K} h_{p+n-z} h_{p-z}$$

so that signal R can be defined as $$R_k = \sum_{n=0}^{K-1} h_k h_{k+n} = h_k * h_{-k}$$

which is the autocorrelation of $h_k$.

On the other hand, in the optimization of $$\frac{\partial L}{\partial \varepsilon_k^{(*)}} = 0$$

we have that:

1.—$k \in l_1$: cuadratic zone:

$$\frac{1}{\delta}(\xi_k + \xi_k^*) - (\beta_k + \beta_k^*) - (\alpha_k + \alpha_k^*) = 0$$

*$\beta_k^{(*)} = 0$ according to KKT, since in the cuadratic zone $\xi_k^{(*)} = 0$

*either $\xi_k$ or $\xi_k^*$ are different than zero, but not at the same time. Therefore:

$$\xi_k^{(*)} = \delta \alpha_k^{(*)}$$

It can be demonstrated that (using $\alpha_k \alpha^*_k = 0$)

$$\frac{1}{2\delta}\sum_{k \in I_1}(\xi_k^2 + \xi_k^{*2}) = \frac{1}{2\delta}\sum_{k \in I_1}(\delta^2 \alpha_k^2 + \delta^2 \alpha_k^{*2}) =$$

$$= \frac{\delta}{2}\sum_{k \in I_1}(\alpha_k^2 + \alpha_k^{*2}) = \frac{\delta}{2}\sum_{k \in I_1}(\alpha_k - \alpha_k^*)^2 =$$

$$= \frac{\delta}{2}(\alpha - \alpha^*)^T I_{I_1}(\alpha - \alpha^*)$$

2.—$k \in I_2$: linear zone. As in the previous case we have:

$$\beta_k^{(*)} = 0 \text{ par } \xi_k^{(*)} \neq 0$$

then, $$\alpha_k^{(*)} = C$$

iv. Solution for the Primal Signal Model

The solution of the primal signal model is depicted in FIG. 1, where given the initial model:

$$v_k = \hat{i}_k * h_k + e_k = \hat{v}_k + e_k$$

whose solution is $$\hat{i}_k = n_k * \hat{h}_k = n_k * h_{-k}$$

we get that $$\hat{v}_k = \hat{i}_k * h_k = n_k * R_k^h$$

v. Dual Signal Model

Be the set of measurements $\{v_k\}$, modeled by a nonlinear regression from a set of given locations (k). This regression uses a nonlinear transformation $\varnothing: R \rightarrow H$, which maps the set of locations (real scalars) to a Reproducing Hilbert Kernel Space (RKSH) H, or feature space. By choosing an adequate $\phi$, we can build a linear regression model in H, given by:

$$v_k = \langle w, \phi(k) \rangle + e_k$$

where $w \in H$ is the weight vector.

vi. Primal Problem for the Dual Signal Model

By developing the primal problem, functional is given by:

$$J_{DSM} = \sum_{k=0}^{K-1}\frac{w_k^2}{2} + \frac{1}{2\delta}\sum_{k \in I_1}(\xi_k^2 + \xi_k^{*2}) + C\sum_{k \in I_2}(\xi_k + \xi_k^*) - \frac{1}{2}\sum_{k \in I_2}\delta C^2$$

To be minimized with respect to $\{\omega_l\} y\{\epsilon_k^{(*)}\}$, and constrained to:

$$v_l - \langle w, \phi(l) \rangle \leq \epsilon + \xi_l$$

$$-v_l + \langle w, \phi(l) \rangle \leq \epsilon + \xi^*_l$$

$$\xi_l, \xi^*_l \geq 0$$

By obtaining the Lagrangian and taking the derivatives with respect to primal variables, we get to:

$$w = \sum_{k=0}^{K-1} \eta_k \phi(k)$$

Hence, voltage can be expressed as $$v_k = \left\langle \sum_{j=0}^{K-1} \eta_j \phi(j), \phi(k) \right\rangle = \sum_{j=0}^{K-1} \eta_j \langle \phi(j), \phi(k) \rangle$$

And by using the kernel trick, $$v_k = \sum_{j=0}^{K-1} \eta_j \mathcal{K}(j, k) = \sum_{j=0}^{K-1} \eta_j \mathcal{K}(j - k)$$

This last equality is fulfilled as far as K is given by a suitable Mercer kernel.

vi. Dual Problem for the Dual Signal Model

By defining $$G(j,k) = \langle \phi(j), \phi(k) \rangle = k(j,k)$$

where the following functional has to be maximized:

$$L_D = -\frac{1}{2}(\alpha - \alpha^*)^T(G + \delta I)(\alpha - \alpha^*) + v^T(\alpha - \alpha^*) - \varepsilon 1^T(\alpha + \alpha^*)$$

$$0 \leq \alpha^{(*)} \leq C$$

and taking into account the convolutional model, then the voltage recorded in different K points $\{k=0, \ldots, K-1\}$ is $$v_k = \sum_{j=0}^{K-1} i_j h_{j-k}$$

Comparing the equations of $v_k$, and identifying terms, we can express $$K(j-k) = h_{j-k}$$

$$\hat{i}_k = n_k$$

and then, $$\hat{v}_k = n_k * K_k = n_k * h_k$$

Therefore, taking $\hat{i}(k) = n(k)$ we find that the convolutive model emerges naturally for the relationship between the impulse response and the sparse signal (some few samples are different from zero).

The invention claimed is:

1. System for reconstruction and visualization of cardiac electrical activity, comprising:
   a set of catheters configured to measure cardiac voltages with a plurality of electrodes;
   positioning means configured for calculating coordinates of a location of said set of catheters;
   auxiliary imaging means for auxiliary image media acquisition, configured for giving anatomical geometric information of cardiac walls;
   signal processing means for processing signals obtained from the set of catheters, wherein said processing means implement an algorithm based on Support Vector Machines (SVM) for resolving a signal problem, incorporating information about a transfer function of the cardiac electrical activity from cardiac cells to the catheters, by an SVM kernel;

the signal processing means being coupled to interpolating means, configured for making use of spatial redundancy and improving resolution without needing matrix inversions; and visualizing means for visualizing a processed signal.

2. System of reconstruction of the cardiac activity according to claim 1, wherein the auxiliary image media are at least one selected among:

resonance;
computer axial tomography;
echography;
scopy.

3. System for reconstruction of the cardiac activity according to claim 1, wherein the auxiliary image media detect additional cardiac electric properties.

4. System for reconstruction of the cardiac activity according to claim 1, wherein the system detects regions of necrosis.

5. System for reconstruction of the cardiac activity according to claim 1, wherein the SVM includes a statistical learning algorithm, derived from the structural risk minimization principle.

6. System for reconstruction of the cardiac electric activity according to claim 1, wherein the signals are the voltages measured in a k-th electrode of the plurality of catheters, and are acquired in the same time instant for all the catheters.

7. System for reconstruction of cardiac activity, according to claim 1, wherein one of the signals is calculated by using the volume conductor equation for a homogeneous media.

8. System for reconstruction of cardiac activity according to claim 1, wherein media for catheter location record the spatial coordinates of each catheter.

9. System for reconstruction of cardiac activity, according to claim 1, wherein media for auxiliary image of the system comprise data of geometry of a cardiac cavity.

10. System for reconstruction of cardiac activity, according to claim 1, wherein the system includes interpolation and decimation media, for yielding an increment in accuracy given by a given number of sensing catheters.

* * * * *